United States Patent [19]
Anis

[11] Patent Number: 4,878,911
[45] Date of Patent: Nov. 7, 1989

[54] FLEXIBLE ONE-PIECE POSTERIOR CHAMBER LENS

[76] Inventor: Aziz Y. Anis, 7531 N. Hampton, Lincoln, Nebr. 68506

[21] Appl. No.: 248,236

[22] Filed: Sep. 19, 1988

Related U.S. Application Data

[63] Continuation of Ser. No. 67,163, Jun. 29, 1987, abandoned, which is a continuation-in-part of Ser. No. 44,753, May 1, 1987, Pat. No. 4,804,361, and a continuation-in-part of Ser. No. 201,388, May 17, 1988, which is a continuation of Ser. No. 624,232, Jun. 25, 1984, abandoned.

[51] Int. Cl.4 ............................................. A61F 2/16
[52] U.S. Cl. ...................................................... 623/6
[58] Field of Search ............................................ 623/6

[56] References Cited

U.S. PATENT DOCUMENTS

| 4,402,579 | 9/1983 | Poler | 623/6 X |
| 4,424,597 | 1/1984 | Schlegel | 623/6 |
| 4,439,873 | 4/1984 | Poler | 623/6 |

FOREIGN PATENT DOCUMENTS

| 1103399 | 5/1955 | France | 623/6 |
| 8500527 | 1/1986 | Netherlands | 623/6 |
| 2124500A | 2/1984 | United Kingdom | 623/6 |
| 2151371A | 7/1985 | United Kingdom | 623/6 |

Primary Examiner—Ronald L. Frinks

[57] ABSTRACT

A posterior chamber lens implant comprising a flexible, substantially ring-shaped position fixation member which extends around a lens body. A pair of posts extend oppositely from the lens body to the position fixation member to cause the lens body to be centrally positioned with respect to the lens body. The relationship of the position fixation member and the posts permits the fixation member to be compressed towards the lens body to enable the implant to be inserted in the eye.

6 Claims, 2 Drawing Sheets

FLEXIBLE ONE-PIECE POSTERIOR CHAMBER LENS

CROSS REFERENCE TO RELATED APPLICATION

This application is a continuation of application Ser. No. 067,163 filed June 29, 1987, now abandoned, which in turn is a continuation-in-part of application Ser. No. 044,753 filed May 1, 1987, now U.S. Pat. No. 4,804,361. This application is also a continuation-in-part of U.S. application Ser. No. 201,388 filed May 17, 1988 for FLEXIBLE POSTERIOR CHAMBER LENS, which in turn is a continuation of U.S. application Ser. No. 624,232 filed June 25, 1984 to Aziz Y. Anis, now abandoned.

BACKGROUND OF THE INVENTION

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are enumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view in as much as it cannot properly refract incident light rays. Aphakic correction may be accomplished in three ways:
(1) thick eye glasses worn in front of the eye;
(2) contact lenses worn on the eye, or
(3) artificial intraocular lens implant within the eye.

It is this latter procedure with which the instant invention is concerned.

The structure and procedure of installing an intraocular lens is very critical because of the elements which make up the eye are extremely sensitive and subject to irreparable damage. Numerous experimental lens designs have been abandoned through the years because they caused corneal damage and other manifestations of intraocular irritation. For example, in the late 1940's and early 1950's, H. Ridley conducted clinical experiments with an artificial intraocular lens which included a lens portion having foot-like projections extending radially away therefrom. This device was placed in the posterior chamber with the feet extending between the ciliary processes and the base of the iris. The lens proved positionally unstable and resulted in unsatisfactory amounts of irritation.

Many attempts have been made to provide a satisfactory intraocular lens. In an effort to remedy the problems associated with the prior art lens implants, applicant previously has been granted U.S. Pat. Nos. 4,143,427; 4,166,293; 4,251,887 and 4,575,374.

In the co-pending application, three different lens configurations were described. The instant invention involves a further development of the lens of the co-pending application.

Therefore, it is a principal object of this invention to provide an improved posterior chamber lens.

A further object of the invention is to provide a posterior chamber lens wherein a ring-shaped member extends around a centrally positioned lens body with connecting members extending between the lens body and the fixation member.

Yet another object of the invention is to provide a lens of the type described which is of one-piece construction.

Still another object of the invention is to provide a lens of the type described including a ring-shaped position fixation member which may be compressed relative to the centrally positioned lens body to enable the implant to be inserted into the capsular bag.

Still another object of the invention is to provide a posterior chamber lens which will remain in place even if pressure or force is inadvertently applied to one portion of the lens.

These and other objects will be apparent to those skilled in the art.

SUMMARY OF THE INVENTION

A posterior chamber lens implant is described which may be implanted in the eye after the natural lens of the eye has been removed. In the preferred embodiment of the invention, a flexible, ring-shaped fixation member extends around a lens body which has a diameter less than the position fixation element. A pair of closing opposing connectors extend from the lens body to the position fixation member. The position fixation member may dwell in a single plane or may be concave shaped. The lens may be positioned on either the posterior or anterior side of the position fixation element. The lens body may assume any convenient configuration.

DESCRIPTION OF THE PREFERRED EMBODIMENT

Figure 1:
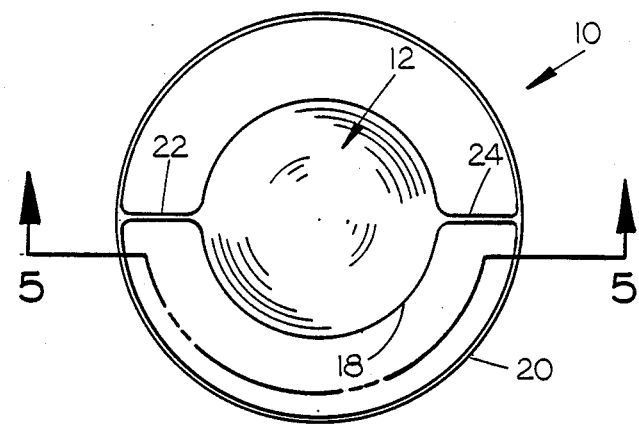
FIG. 1 is an elevational view of the invention.
Figure 4:
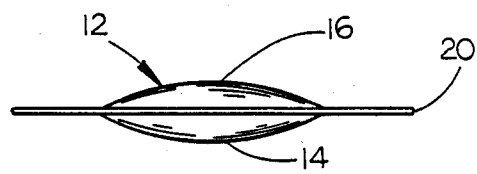
FIG. 4 is an end view of the lens of FIG. 1.
Figure 5:
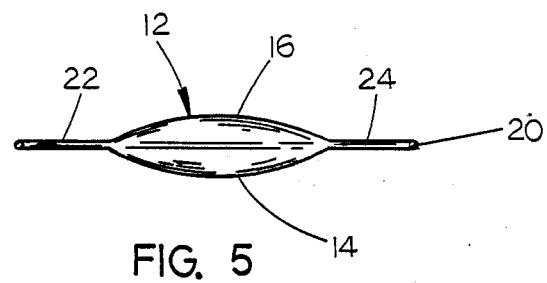
FIG. 5 is a sectional view of the embodiment of FIG. 1.

The lens implant of this invention is referred to generally by the reference numeral 10. Lens implant 10 includes a disc-shaped lens body 12 which may be of the convex-plano, convex-convex, or any other convenient configuration. For purposes of description, lens body 12 will be described as having a front or anterior face 14, back or posterior face 16 and peripheral edge 18. The preferred embodiment is illustrated in FIGS. 1, 4 and 5 although the embodiment illustrated in FIGS. 2 and 3 may be utilized as well.

A ring-shaped position fixation member 20 is positioned outwardly of the lens body 12 and is connected thereto by a pair of opposing posts 22 and 24 which extend oppositely from the lens body 12. Preferably, lens body 12 has a diameter of 6 millimeters but the same can be between 4.0 and 8.0 millimeters. Preferably, the diameter of the ring forming fixation member 20 is 10.5 millimeters but the same can vary between 8.0 millimeters and 13.0 millimeters. Preferably, the diameter of the cross section through the fixation member 20 is 0.15 millimeters.

The construction of the lens implant 10 is such that the ring-shaped fixation member 20 will engage the capsular bag for 360°. The connecting posts 22 and 24 aid in centrally positioning the lens body 12 with respect to the fixation member 20 and adds stability to the lens implant. The construction of the lens implant 10 is such that the fixation member 20 may be compressed towards the lens body 12 between the connecting posts 22 and 24.

Figure 2:
FIG. 2 is an end view of the embodiment of the invention.
Figure 3:
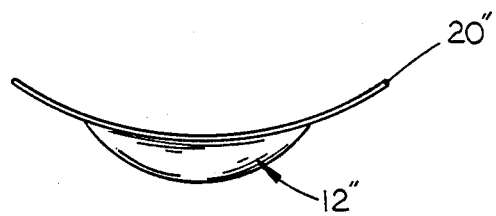
FIG. 3 is a end view of a further embodiment of the invention.

FIGS. 2 and 3 illustrate the fact that the fixation member 20' may be curved as desired. FIGS. 2 and 3 also illustrate that the lens body 12' may be positioned posteriorly of the fixation member 20' or anteriorly of the position fixation member 20'.

Figure 6:
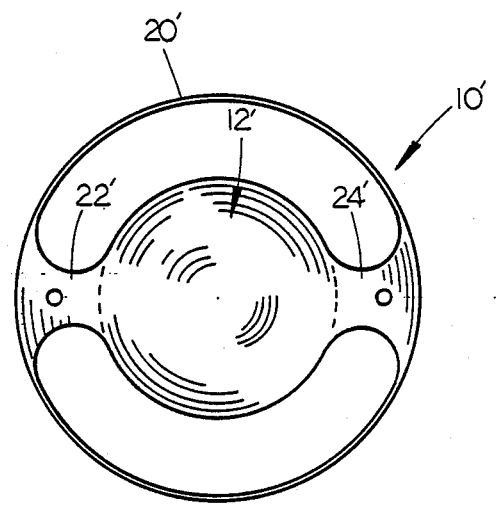
FIG. 6 is an elevational view of a modified form of the invention.

FIG. 6 illustrates a modification of the invention and is referred to by the reference numeral 10'. Lens implant 10' includes a disc-shaped lens body 12' which may be of the convex-plano, convex-convex, or any other convenient configuration. Lens implant 10' is identical to lens implant 10 except that the posts 22' and 24' have a greater width than the posts 22 and 24. By increasing the width of the posts 22' and 24', it is believed that greater stability of the lens implant is achieved. During implantation, the fixation member 20' will be compressed towards the lens body 12' and the posts 22' and 24' prevent the fixation member 20' from "bulging out" in the vicinity of the posts.

In all of the embodiments, the lens may be inserted in any position within the eye since there is not a top or bottom portion of the lens implant. The 360° engagement of the fixation member 20 with the eye positively ensures that the lens implant will remain in position and will not become inadvertently dislodged.

Thus it can be seen that the invention accomplishes at least all of its stated objectives.

I claim:

1. A one-piece intraocular lens implant, comprising:
   a flexible, substantially ring-shaped position fixation member having a diameter of between 8.0 and 13.0 millimeters wherein the fixation member, after implantation of the lens implant, engages the capsular bag for 360 degrees;
   a lens body having a diameter of between 4.0 and 8.0 millimeters, but less than said position fixation member and being positioned within said position fixation member; and
   connection means connecting said lens body with said position fixation member, including no more than two members which extend oppositely from said lens body, said connection means being adapted to permit compression of opposing sides of said fixation member intermediate said post members inwardly to the lens body.

2. The lens implant of claim 1 wherein said position fixation member dwells in a single plane.

3. The lens implant of claim 1 wherein said position fixation member dwells in a flat plane with said lens body and connection means and the lens body being curved posteriorly with respect to the fixation member.

4. The lens implant of claim 1 wherein said position fixation member has an anterior side and a posterior side, said lens body being positioned at the anterior side of said position fixation member.

5. The lens implant of claim 1 wherein said position fixation member has an anterior side and a posterior side, said lens body being positioned at the posterior side of said position fixation member.

6. The lens implant of claim 1 wherein said position fixation member is a closed, generally circular ring.

* * * * *